(12) United States Patent
Costin

(10) Patent No.: US 6,436,926 B1
(45) Date of Patent: Aug. 20, 2002

(54) COMPOSITIONS AND METHODS FOR TREATING SUPERFICIAL FUNGAL INFECTIONS

(75) Inventor: James C. Costin, Belle Mead, NJ (US)

(73) Assignee: MedPointe, Inc., Somerset, NJ (US)

( * ) Notice: Subject to any disclaimer, the term of this patent is extended or adjusted under 35 U.S.C. 154(b) by 0 days.

(21) Appl. No.: 09/945,638

(22) Filed: Sep. 4, 2001

Related U.S. Application Data

(62) Division of application No. 09/568,635, filed on May 10, 2000, now abandoned.
(60) Provisional application No. 60/133,283, filed on May 10, 1999.

(51) Int. Cl.[7] ............................................... A61K 31/54
(52) U.S. Cl. .................... 514/222.5; 514/858; 514/860; 514/864; 514/880; 514/881
(58) Field of Search ............................... 514/222.5, 858, 514/860, 864, 880, 881

(56) References Cited

U.S. PATENT DOCUMENTS

| 5,650,145 A | 7/1997 | Saint-Leger ................ 424/70.1 |
| 6,011,030 A | 1/2000 | Pfirmann .................. 514/222.2 |

OTHER PUBLICATIONS

Chemical Abstracts 121:17719, Taurolidine as hair treatment agent (May 1994).

*Primary Examiner*—Frederick Krass
(74) *Attorney, Agent, or Firm*—Elliot M. Olstein; Raymond E. Stauffer

(57) ABSTRACT

Compositions comprising 4,4'-methylenebis(tetrahydro-1,2, 4-thiadiazine) 1,1,1',1',-tetraoxide and their use in treating dermatologic disorders are disclosed.

14 Claims, No Drawings

COMPOSITIONS AND METHODS FOR TREATING SUPERFICIAL FUNGAL INFECTIONS

This application is a divisional of U.S. Ser. No. 09/568,635, filed May 10, 2000 and now abandoned, and claims the benefit of priority of U.S. Provisional Application 60/133,283, filed May 10, 1999.

The present invention relates to novel compositions and their use in the treatment of dermatologic disorders. More particularly, the present invention relates to compositions which contain 4,4'-methylenebis(tetrahydro-1,2,4-thiadiazine) 1,1,1',1',-tetraoxide, known generically as taurolidine, as an active ingredient and the use of such compositions in the topical treatment of superficial fungal infections.

Superficial infections are caused by fungi that invade dead tissues of the skin or its appendages (stratum corneum, nails, hair). Microsporum, Trichophyton, and Epidermophyton are the genera most commonly involved in superficial infections. Some of these dermatophytes produce mild or no inflammation; in such cases, the organism may persist indefinitely, causing intermittent remissions and exacerbations. In other cases an acute infection may occur upon onset of the infection, typically causing a sudden vesicular and bullous disease of the feet or an inflamed boggy lesion of the scalp (kerion) that is due to a strong immunologic reaction to the fungus; properly treated acute infection is usually followed by remission or cure.

Since clinical differentiation of the related dermatophytes can be difficult, these infections are more conveniently discussed with reference to the sites involved.

*Tinea corporis* (ringworm of the body) is usually caused by a Trichophyton. The characteristic pink-to-red papulosquamous annular lesions have raised borders, expand peripherally, and tend to clear centrally.

*Tinea pedis* (ringworm of the feet; athlete's foot) is common. Trichophyton mentagrophytes infections begin in the $3^{rd}$ and $4^{th}$ interdigital spaces and later involve the plantar surface of the arch. The toe web lesions often are macerated and have scaling borders; they may be vesicular. Acute flare-ups, with many vesicles and bullae, are common during warm weather. Infected toenails become thickened and distorted. *T. rubrum* produces a scaling and thickening of the soles, often extending just beyond the plantar surface in a "moccasin" distribution. Itching, pain, inflammation, or vesiculation with concomitant itching or pain may be slight or severe. *Tinea pedis* may be complicated by secondary bacterial infection, cellulitis, or lymphangitis, sometimes of a recurrent nature. *Tinea pedis* may be confused with maceration (from hyperhidrosis and occlusive footgear), with contact dermatitis (from sensitivity to various materials in shoes, particularly adhesive cement), with eczema or with psoriasis.

*Tinea unguium* (ringworm of the nails), a form of onychomycosis, is usually caused by a Trichophyton species. Toenail involvement is common in long-standing tinea pedis; infections of the fingernails are less common. The nails become thickened and lusterless, and debris accumulates under the free edge. The nail plate becomes separated and the nail may be destroyed. Differentiating a Trichophyton infection from psoriasis is particularly important because chemotherapy is specific and prolonged treatment is required.

*Tinea capitis* (ringworm of the scalp) mainly affects children. It is contagious and may become epidemic. *Trichophyton tonsurans* infection has become the common cause in the USA; other Trichophyton species (e.g., *T. violaceum*) are common in other parts of the world. *T. tonsurans* infection of the scalp is subtle in onset and characteristics. Inflammation is low-grade and persistent; the lesions are neither annular nor sharply marginated, and the hairs do not fluoresce under Wood's light. Affected areas of the scalp show characteristic black dots resulting from broken hairs. The fungus, an endothrix, produces chains of arthrospores that can be seen microscopically within the hair. Trichophyton species may persist in adults.

Microsporum audouinii and *M. canis,* once predominant, are much less common causes of tinea capitis in the USA. *M. audouinii* lesions are small, scaly, semi-bald grayish patches of broken, lusterless hairs. Infection may be limited to a small area or extend and coalesce until the entire scalp is involved, sometimes with ringed patches extending beyond the scalp margin. *M. canis* and *M. gypseum* usually cause a more inflammatory reaction, with shedding of the infected hairs. A raised, inflamed, boggy granuloma (kerion) may also occur; it is followed shortly by healing. Diagnosis of a Microsporum infection is facilitated by examining the scalp under Wood's light; infected hairs may fluoresce a light, bright green. The organism is an ectothrix, producing spores to form a sheath around the hair. The sheath can be seen on microscopy. Culture of the fungus is also important in establishing the diagnosis.

*Tinea cruris* (jock itch), far more common in males, may be caused by various dermatophyte or yeast organisms. Typically, a ringed lesion extends from the crural fold over the adjacent upper inner thigh. Both sides may be affected. Scratch dermatitis and lichenification are often seen. Lesions may be complicated by maceration, miliaria, secondary bacterial or candidal infection, and reactions to treatment. Recurrence is common, since fungi may persist indefinitely on the skin or may repeatedly infect susceptible individuals. Flare-ups occur most often during the summer. Tight clothing or obesity tends to favor growth of the organisms. The infection may be confused with contact dermatitis, psoriasis, erythrasma, or candidiasis. The scrotum is often acutely inflamed in candidal intertrigo, whereas in dermatophyte infections scrotal involvement is usually absent or slight.

We have found that taurolidine has a broad spectrum of activity against the fungi that cause superficial fungal infections such as ringworms (*Tinea corpis* and *capitis*), athlete's foot (*Tinea pedis*), nail infections (onychomycosis), and "jock itch" (*Tinea cruris*).

The broad spectrum of activity of taurolidine against the clinically revelant fungi is set forth in Table 1. Where with the exception of Candida albicans (>5 mg/ml) it has been found that the antifungal activity of taurolidine is approximately equivalent to its antibacterial activity (0.3–0.6 mg/ml).

TABLE 1

Sensitivity of Fungi to Taurolidine

| Organisms | Concentration of Taurolin (mg/ml) | | | | | | MIC (mg/ml) | |
| --- | --- | --- | --- | --- | --- | --- | --- | --- |
| | 5 | 2.5 | 1.25 | 0.625 | 0.3 | Control | | |
| C. albicans (Has. A) | + | ++ | +++ | +++ | +++ | +++ | >5 | |
| C. albicans (I) | + | +++ | +++ | +++ | +++ | +++ | >5 | |
| C. albicans (Jones) | ++ | +++ | +++ | +++ | +++ | +++ | >5 | |
| C. albicans (Wilton) | ++ | +++ | +++ | +++ | +++ | +++ | >5 | |
| Candida spp. | − | − | − | ++ | +++ | +++ | 1.25 | |
| Aspergillus fumigatus I | − | − | − | − | ++ | +++ | 0.625 | |
| Aspergillus fumigatus II | − | − | − | + | ++ | +++ | 1.25 | Solid Medium |
| Aspergillus fumigatus III | − | − | − | − | ++ | +++ | 0.625 | |
| Aspergillus niger | − | − | − | + | ++ | +++ | 1.25 | |
| Trichophyton mentagrophytes | − | − | − | − | − | +++ | <0.3 | |
| Epidermophyton floccosum | − | − | − | − | − | ++ | <0.3 | |
| Mucor spp. (Lane) | − | − | − | − | ++ | +++ | 0.625 | |
| Rhizopus spp. | − | − | − | − | ++ | +++ | 0.625 | |
| Sporotrichum schenkii | − | − | − | ± | ++ | +++ | 0.625 | |
| Cryptococcus neoformans | − | − | − | − | − | ++ | <0.3 | |
| C. albicans (Has. A) | − | − | ++ | +++ | +++ | +++ | 2.5 | |
| C. albicans (Jones) | − | ++ | ++ | ++ | ++ | +++ | 5 | Liquid Medium |
| C. spp. | − | − | − | − | ++ | +++ | 0.625 | |
| C. tropicalis | − | − | − | − | ± | ++ | 0.3 | |
| Mucor spp. (heavy inoc.) | − | − | − | ± | ++ | +++ | 0.625 | |
| Mucor spp. (light inoc.) | − | − | − | − | + | ++ | 0.625 | |
| Aspergillus fumigatus | − | − | − | − | ± | ++ | 0.3 | |
| Trichophyton rubrum | − | − | − | − | ± | ++ | 0.3 | |

The present invention relates to the use of 4,4'-methylenebis(tetrahydro-1,2,4-thiadiazine)-1,1,1',1' tetraoxide to treat superficial fungal infections.

Taurolidine occurs as a white to off-white powder having the molecular formula $C_7H_{16}N_4O_4S_2$ and a melting point of 154–158° C.

Taurolidine's general characteristics include acceptable stability in the solid state when stored at ambient conditions, melting with decomposition at approximately 170° C. and the following solubility in aqueous solutions and organic solvents.

| Water | 1% at 20° C. |
| --- | --- |
| Dilute HCl | soluble |
| Dilute NaOH | soluble |
| CHCl$_3$ | insoluble |
| EtOH | sparingly soluble |
| DMF | 1 g in 2 mL/ca. 60° C. |
| Acetone | 1 g in 120 mL/Boiling |
| Ethanol | 1 g in 130 mL/Boiling |
| Methanol | 1 g in 170 mL/Boiling |
| Ethyl Acetate | 1 g in 200 mL/Boiling |

A saturated solution of taurolidine in deionized water has a pH of 7.4. The apparent partition coefficient of taurolidine between octanol and water (buffered at pH 7.2) is approximately 0.13 and would therefore not be predicted to accumulate to any significant extent in fatty tissues.

The synthesis of taurolidine is covered in a number of patents including U.S. Pat. No. 3,423,408; Switzerland No. 482,713 and United Kingdom No. 1,124,285 and is carried out in five stages:

Potassium phthalimidoethane sulphonate is prepared from taurine, phthalic anhydride, glacial acetic acid and potassium acetate;

Potassium phthalimidoethane sulphonate is then converted to phthalimidoethane sulphonylchloride by chlorination with phosphorous oxychloride;

Phthalimidoethane sulphonylchloride is reacted with ammonia to form phthalimidoethane sulphonamide;

Phthalimidoethane sulphonylchloride is reacted with hydrazine hydrate and in the subsequent hydrazinolysis to form taurinamide hydrochloride; and Taurolidine is prepared from taurinamide hydrochloride and formaldehyde.

The antimicrobial actions of taurolidine have been described in U.S. Pat. No. 3,423,408 and elsewhere in the literature. In addition, the following United States Patents describe various uses for and compositions containing taurolidine: U.S. Pat. No. 4,107,305, treatment of endotoxaemia; U.S. Pat. No. 4,337,251, elimination of adhesion formation as a result of surgery; U.S. Pat. No. 4,587,268, resorbable aqueous gels; U.S. Pat. No. 4,604,391, prevention of the occurrence of osteitis or osteomyelitis; U.S. Pat. No. 4,626,536, combating toxic proteins or peptides in the blood; U.S. Pat. No. 4,772,468, treatment of bone cavities; and U.S. Pat. No. 4,882,149, directed to methods for filling congenital, surgical or traumatic defects with compositions comprising natural bone mineral having absorbed therein/thereon taurolidine.

Taurolidine has been shown to be safe and well tolerated at systemic doses exceeding 40 g/day and cumulative doses up to and exceeding 300 g.

The formulations of taurolidine generally utilized are sterile solutions containing 0.5%, 1.0%, 2.0% or 4.0% taurolidine for irrigation/lavage, wound instillation, or intravenous administration, primarily for the treatment or prevention of peritonitis, sepsis or osteitis/osteomyelitis.

According to the present invention there are provided pharmaceutical compositions comprising taurolidine with one or more carriers or excipients. The compositions preferably take the form of powders, sprays, ointments, gels, pastes, creams, lotions, etc.

The carriers or excipients in such compositions may, for example, be those conventional for such forms and may include gelatin, sterile water, suspending, emulsifying, dispersing, thickening, gelling or flavouring agents, ointment bases or aerosol propellants.

The compositions, and particularly the non-dosage forms such as powders, sprays, gels, pastes, lotions, solutions, ointments, etc., preferably contain the active substance at a concentration between 0.10 and 20.0% by weight, preferably between 0.5 and 2.0% for aqueous solutions or aerosol sprays or up to 10% for powders and ointments.

What is claimed is:

1. A method for the treatment of superficial fungal infections of the skin, stratum corneum, nails or an hair which comprises topically applying to a human or other warm blooded animal in need of such treatment a composition containing a topically effective amount of 4,4-methylenebis (tetrahydro-1,2,4-thiadiazine-1,2-dioxide.

2. The method of claim 1 wherein said composition is a powder.

3. The method of claim 1 wherein said composition is a gel.

4. The method of claim 1 wherein said composition is a paste.

5. The method of claim 1 wherein said composition is an aerosol.

6. The method of claim 1 wherein said composition is a solution.

7. The method of claim 1 wherein said composition is a cream.

8. The method of claim 1 wherein the superficial fungal infection is ringworm.

9. The method of claim 1 wherein the superficial fungal infection is athlete's foot.

10. The method of claim 1 wherein the superficial fungal infection is an infection of the nails.

11. The method of claim 1 wherein the superficial fungal infection is Tinea cruris.

12. The method of claim 1 wherein the superficial fungal infection is of the stratum corneum.

13. The method of claim 1 wherein the superficial fungal infection is an infection of the skin, stratum corneum or nails.

14. The method of claim 1 wherein 4,4-methylenebis (tetrahydro-1,2,4-thiadiazine-1,2-dioxide) is the sole active agent of the composition.

* * * * *